(12) United States Patent
Rutter

(10) Patent No.: US 7,771,446 B2
(45) Date of Patent: *Aug. 10, 2010

(54) BALLOON DILATOR

(76) Inventor: Michael John Rutter, 1110 Brayton Ave., Cincinnati, OH (US) 45215

( * ) Notice: Subject to any disclaimer, the term of this patent is extended or adjusted under 35 U.S.C. 154(b) by 270 days.

This patent is subject to a terminal disclaimer.

(21) Appl. No.: 12/052,983

(22) Filed: Mar. 21, 2008

(65) Prior Publication Data

US 2008/0167608 A1    Jul. 10, 2008

Related U.S. Application Data

(63) Continuation-in-part of application No. 11/533,562, filed on Sep. 20, 2006, now Pat. No. 7,591,830, which is a continuation-in-part of application No. 11/231,457, filed on Sep. 21, 2005, now abandoned.

(51) Int. Cl.
*A61M 29/00* (2006.01)
(52) U.S. Cl. ...................................... 606/191
(58) Field of Classification Search ................ 606/159, 606/167, 170, 174, 191–198; 604/96.01–103.01; 128/207.14, 207.15
See application file for complete search history.

(56) References Cited

U.S. PATENT DOCUMENTS

| | | | |
|---|---|---|---|
| 3,499,450 A | | 3/1970 | Rathjen |
| 3,640,282 A | | 2/1972 | Kamen et al. |
| 3,693,624 A | * | 9/1972 | Shiley et al. ........... 128/207.15 |
| 4,791,923 A | * | 12/1988 | Shapiro ................. 128/207.15 |
| 4,983,167 A | | 1/1991 | Sahota |
| 5,222,966 A | | 6/1993 | Perkins et al. |
| 5,320,634 A | * | 6/1994 | Vigil et al. .................. 606/159 |
| 5,792,158 A | | 8/1998 | Lary |

* cited by examiner

*Primary Examiner*—Kevin T Truong
(74) *Attorney, Agent, or Firm*—Hasse & Nesbitt LLC; Ronald J. Richter; Donald E. Hasse

(57) ABSTRACT

A medical apparatus for widening a stenosis or for deploying a stent in a patient. The apparatus has a central axis and an inflatable outer dumbbell-shaped balloon. The apparatus is insertable into a lumen of a patient for movement of the balloon therein between a deflated configuration and an inflated configuration. The balloon stays in position over the stenosis or the area in need of the stent when it is inflated. The apparatus can include a flexible support member mounted on the external surface of the balloon with at least one microsurgical blade, which forms an effective cutting edge upon inflation of the outer balloon. The apparatus can also include one or more inner balloons that allow higher dilation pressures to be generated from inside the outer balloon. The apparatus can also include a hollow central core that may permit ventilation of the airway during the dilation process.

20 Claims, 3 Drawing Sheets

BALLOON DILATOR

CROSS-REFERENCE TO RELATED APPLICATION

This application is a continuation-in-part of application Ser. No. 11/533,562, filed on Sep. 20, 2006, now U.S. Pat. No. 7,591,830 which is a continuation-in-part of application Ser. No. 11/231,457, filed on Sep. 21, 2005 now abandoned.

FIELD OF THE INVENTION

The present invention relates to medical care for relieving a stenosis or deploying a stent in a patient. In particular, the invention relates to a balloon device for performing dilation of a lumen in a patient's larynx, trachea or bronchi, vascular system, esophagus, or other areas of the body needing such treatment.

BACKGROUND OF THE INVENTION

Management of stenosis of the trachea and bronchi, including laryngotracheal and subglottic stenosis, is one of the most challenging problems for the head and neck surgeon. Subglottic stenosis is a congenital or acquired narrowing of the subglottic airway. In the early twentieth century subglottic stenosis was rare, and most cases occurred in adults. In the 1960's the incidence of acquired subglottic stenosis began to dramatically increase in the neonatal population, most likely the result of increased survival of low-birth-weight infants and the increased use of intubation in this population. In addition, long term intubation has become an accepted alternative to tracheotomy, leading to more and more incidences of tracheal stenosis. Accordingly, the management of this condition has undergone a revolution, and reconstructive surgery efforts have been directed towards this population.

Most patients with stenosis of the airway are referred to and are treated at large academic centers by physicians specially trained in this area. There is a wide range of presentation of subglottic stenosis with similarities and differences in the pediatric age group compared to adults. If the stenosis is severe and congenital, the patient will show signs of airway distress at birth. More commonly, the pediatric patient with subglottic stenosis is a neonate in the intensive care unit who has failed extubation, usually multiple times. Occasionally patients will present in clinic with a tracheotomy and the report of some airway obstruction. Infants with mild subglottic stenosis may present with recurrent croup-like illnesses and poor feeding. Adults usually have a history of prior intubation with symptoms of progressive shortness of breath and noisy breathing.

Airway balloon dilation has been shown to be a safe and effective palliative procedure for treatment of mild congenital and acquired stenosis of the trachea and bronchi. Dilation of luminal human anatomy to treat stenoses can be dated back to the 16$^{th}$ Century with esophageal "bougie" dilation. Specific medical applications of luminal balloon dilation range from alimentary canal and airway dilation to dilation of the vasculature. Airway dilation dates back over 100 years ago with the invention and subsequent use of the first beveled rigid bronchoscopes for stricture management. The use of balloons to dilate airway strictures emerged in the mid-1980's with reports describing more specific utility of this procedure exclusively and in combination with other treatment modalities for airway stenosis. It was not until the early 1990's that the first balloon dilation involving flexible bronchoscopy was described.

Airway balloon dilation can be used to quickly re-establish tracheal or bronchial luminal patency to restore airflow in a way that doesn't cause excessive trauma to the patient. According to Poiseuille's Law, an increase in a tube's radius (such as the trachea or bronchus) can increase airflow by a power of 4 (airflow=radius of the tube$^4$). That is, very small increases in the luminal diameter of the airway can lead to large increases in airflow through the lungs. Literature has reported the use of balloon dilation for the treatment of benign strictures of the airway. Fibrotic strictures, such as those secondary to tuberculosis, long-term endotracheal or tracheostomy tube placement, berylliosis, Wegener's granulomatosis, or sarcoidosis have been shown to be treatable with airway balloon dilation therapy with general success. Additionally, balloon dilation has been useful in treating strictures secondary to major surgical interventions such as lung transplantation, sleeve resection, bronchial re-implantation, and lobectomy. For the purpose of treating strictures secondary to malignant obstruction, dilation therapy can be used alone or in combination with other techniques such as surgical resection, cryotherapy, laser therapy, and stent placement, depending on the desired outcome for the patient.

Treatment with airway dilation can involve the clinician inserting increasingly larger tubes into the airway (e.g. endotracheal tubes or cat-tail (bougie) dilators), which creates significant shear forces on the airway mucosa. Although safe when performed by a skilled clinician, such a procedure sometimes induces unwanted trauma to the airway in the form of deep lacerations and hemoptysis. Further, current dilation practices do not permit dilation of a tracheal stenosis that is distal to a narrowing of the proximal airway (i.e. a mild subglottic stenosis).

Current airway balloon dilation procedures are typically carried out using angioplasty balloons; however, several limitations to the use of angioplasty balloons become evident when used on the airway. For example, it may be difficult to adequately ventilate the patient during the dilation period, since the typical angioplasty balloon does not include a connection to an oxygen source. Further, the shape of the angioplasty balloon may predispose the balloon to slide out of place during dilation, or the balloon may be limited to the amount of pressure that can be applied before the balloon bursts. Also, the typical angioplasty balloon can usually stretch the airway lumen but not permanently dilate it. Other factors associated with failure of airway balloon dilation include previous attempts at endoscopic repair, circumferential scarring, and loss of cartilaginous support.

In light of the foregoing, it would be advantageous to provide a balloon dilator for the airway of a patient that is able to allow ventilation of the patient during balloon inflation. It would also be helpful to provide an airway balloon dilator that can provide increased inflation pressures during balloon dilation of the airway without balloon rupture. Further, it would be beneficial to provide a balloon that will not slip out of place in the patient's airway or other body lumens during balloon inflation. Finally, it is desirable to provide a balloon dilator that is capable of controlled cutting of scar tissue.

SUMMARY OF THE INVENTION

The present invention provides a balloon dilator for use to quickly re-establish luminal patency to restore flow of air or fluids in a way that avoids excessive trauma to the patient.

In one aspect, the invention provides an apparatus for performing a balloon dilation procedure at the site of a stenosis or for deploying a stent in a patient, the apparatus comprising a central axis and an inflatable outer dumbbell-shaped balloon having an external surface, the apparatus being insertable into a lumen of a patient for movement of the balloon therein between a deflated configuration and an inflated configuration.

Another aspect of the invention provides a method for performing a balloon dilation procedure at the site of a stenosis or for deploying a stent in a lumen of a patient, the method comprising the steps of: (1) inserting an apparatus into the lumen, the apparatus comprising a central axis and an inflatable outer dumbbell-shaped balloon having an external surface, the apparatus being insertable into the lumen of a patient for movement of the balloon therein between a deflated configuration and an inflated configuration, (2) advancing the apparatus within the lumen until the dumbbell-shaped balloon is positioned within the area of the stenosis or the area in need of the stent, and (3) inflating the dumbbell-shaped balloon to cause and allow the external surface of the balloon to expand upon and dilate the area of the stenosis or the area in need of the stent.

Another aspect of the invention provides an apparatus for performing a balloon dilation procedure at the site of a stenosis or for deploying a stent in a patient, the apparatus comprising a central axis; an inflatable dumbbell-shaped outer balloon having an external surface; at least one inflatable inner balloon; a flexible support member mounted along the central axis of the apparatus and on the external surface of the outer balloon, the flexible support member being substantially compliant with the external surface of the outer balloon during movement therewith; and at least one microsurgical blade attached to the support member and adapted to form an effective cutting edge upon inflation of the outer balloon; the apparatus being insertable into the lumen of a patient for movement of the balloons therein between a deflated configuration and an inflated configuration, the at least one inner balloon configured to inflate inside the outer balloon yet separately from the outer balloon, the dumbbell shape of the outer balloon adapted to hold the outer balloon in position over the site of the stenosis or the area in need of the stent, and the at least one blade adapted to form an effective cutting edge upon inflation of the outer balloon.

The nature and advantages of the present invention will be more fully appreciated from the following drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

The present invention provides an apparatus for performing a balloon dilation procedure at the site of a stenosis or for deploying a stent in a patient, the apparatus comprising a central axis and an inflatable outer dumbbell-shaped balloon having an external surface, the apparatus being insertable into a lumen of a patient for movement of the balloon therein between a deflated configuration and an inflated configuration. While the invention will generally be described in terms of an apparatus and method for performing an airway balloon dilation procedure, the apparatus and method are more broadly applicable for use in treating any stenosis or area in need of a stent in a patient. In particular, the invention may be used for performing dilation of a lumen in a patient's larynx, trachea or bronchi, vascular system, esophagus, or other areas of the body.

One aspect of the invention provides an apparatus for performing an airway balloon dilation procedure at the site of a stenosis in the airway of a patient. The apparatus comprises a balloon that when deflated has a narrow diameter, but inflates in a dumbbell shaped fashion whereby the proximal and distal aspects of the balloon inflate before the central aspect of the balloon. This can be achieved by providing the central half of the balloon with a greater wall thickness than the proximal and distal aspects of the balloon. The advantage of this configuration is that once the balloon is employed across a stenosis and inflated, the proximal and distal ends inflate on either side of the stenosis and prevent slipping of the balloon. As pressure inside the balloon increases, the central aspect of the balloon then inflates, expanding the stenosis. When the dumbbell-shaped balloon is fully inflated, it typically has a substantially uniform diameter from its proximal end to its distal end. This apparatus and method would also benefit placement of expandable stents, whereby a stent placed over the central aspect of the balloon would not be able to slip off the balloon once the proximal and distal aspects of the balloon are inflated, locking the stent in position over the central aspect of the balloon. While the present invention is particularly useful as an airway dilator, it is also useful in other areas of the body where balloon slippage is undesirable or where stent deployment is desirable.

Another aspect of the invention provides an apparatus for performing an airway balloon dilation procedure at the site of a stenosis in the airway of a patient, the apparatus comprising a balloon with an outer membrane and optional inner balloons that allow greater radial pressure to be applied, exceeding the rated burst pressure of similar diameter balloons, due to the inner balloons being of smaller radius when inflated than the outer balloon.

Figure 1:
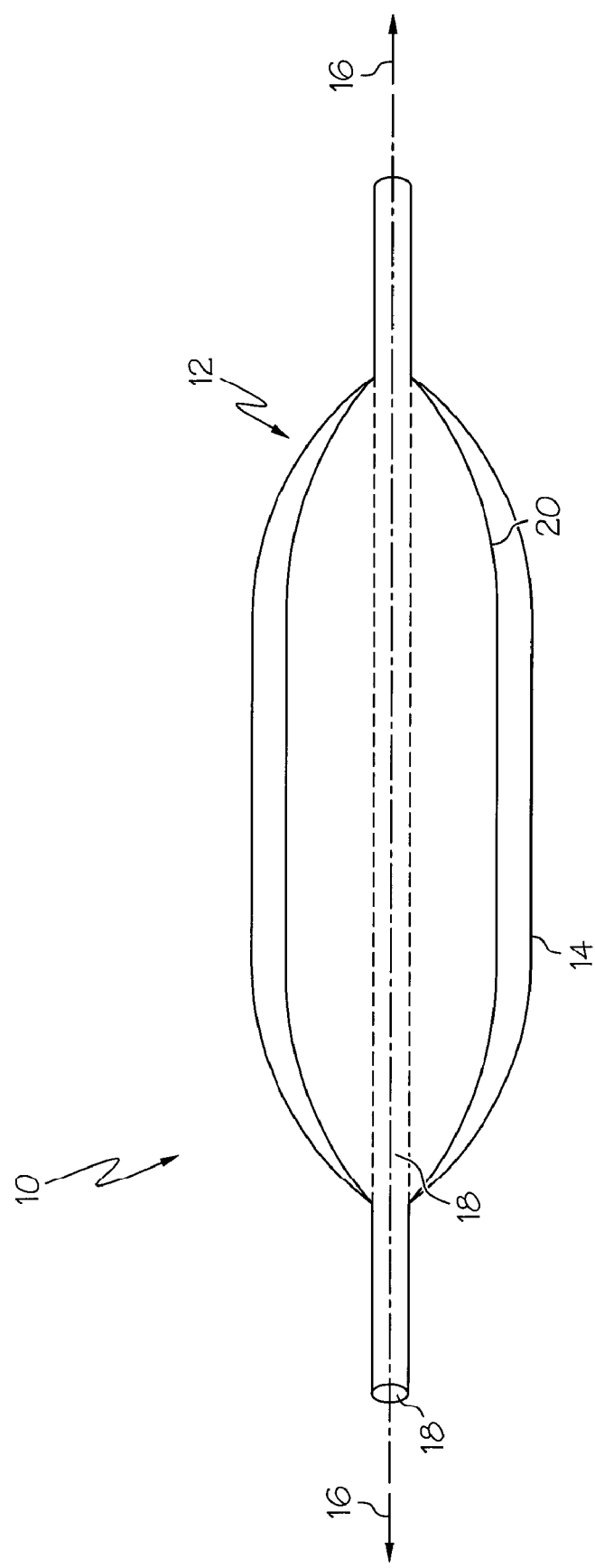
FIG. 1 is a perspective view of one embodiment of the balloon dilator of the present invention.

As illustrated in FIG. 1, one embodiment of the present invention is an apparatus 10 for performing a balloon dilation procedure at the site of a stenosis in the airway of a patient, the apparatus comprising an inflatable outer balloon 12 which has an external surface 14. The apparatus also comprises a central axis 16, a hollow core 18, and at least one inflatable inner balloon 20 adapted to inflate inside the outer balloon 12. The apparatus 10 is typically insertable into the airway of a patient for movement of the balloons 12, 20 between a deflated configuration and an inflated configuration. Further, the inner balloon 20 is designed to inflate inside the outer balloon 12 yet separately from the outer balloon, adding the ability of the apparatus to produce high dilation pressures without balloon rupture.

As shown in FIG. 1, the hollow core 18 traverses the entire apparatus 10. Typically the hollow core connects via a proximal ISO connector to an oxygen source such as an anesthesia circuit or the like, and is designed to allow the patient to be ventilated upon inflation of the balloons during the procedure, when the airway is otherwise occluded. The hollow core 18 is typically in the form of a central ventilating tube which is necessarily strong to prevent the pressure of the balloons from crushing the ventilating tube. The structure of the hollow core 18 is typically similar to a small endotracheal tube with a dilating cuff, and the tube may be reinforced, e.g. with wire, in the area of the cuff.

While standard balloon dilators typically have a very small central lumen to permit passage of a guidewire only, the balloon dilator of the present invention can have a fairly rigid (e.g. wire-reinforced) and relatively large central hollow core that can permit limited ventilation. For example, an 8.0 mm balloon dilator (i.e. having an outer diameter of 8.0 mm when inflated) can have a central ventilating lumen with a 2.0 mm inner diameter and a 3.0 mm outer diameter, while a 16 mm balloon dilator can have a central ventilating core with a 4.0 mm inner diameter and a 5.5 mm outer diameter.

Figure 2:
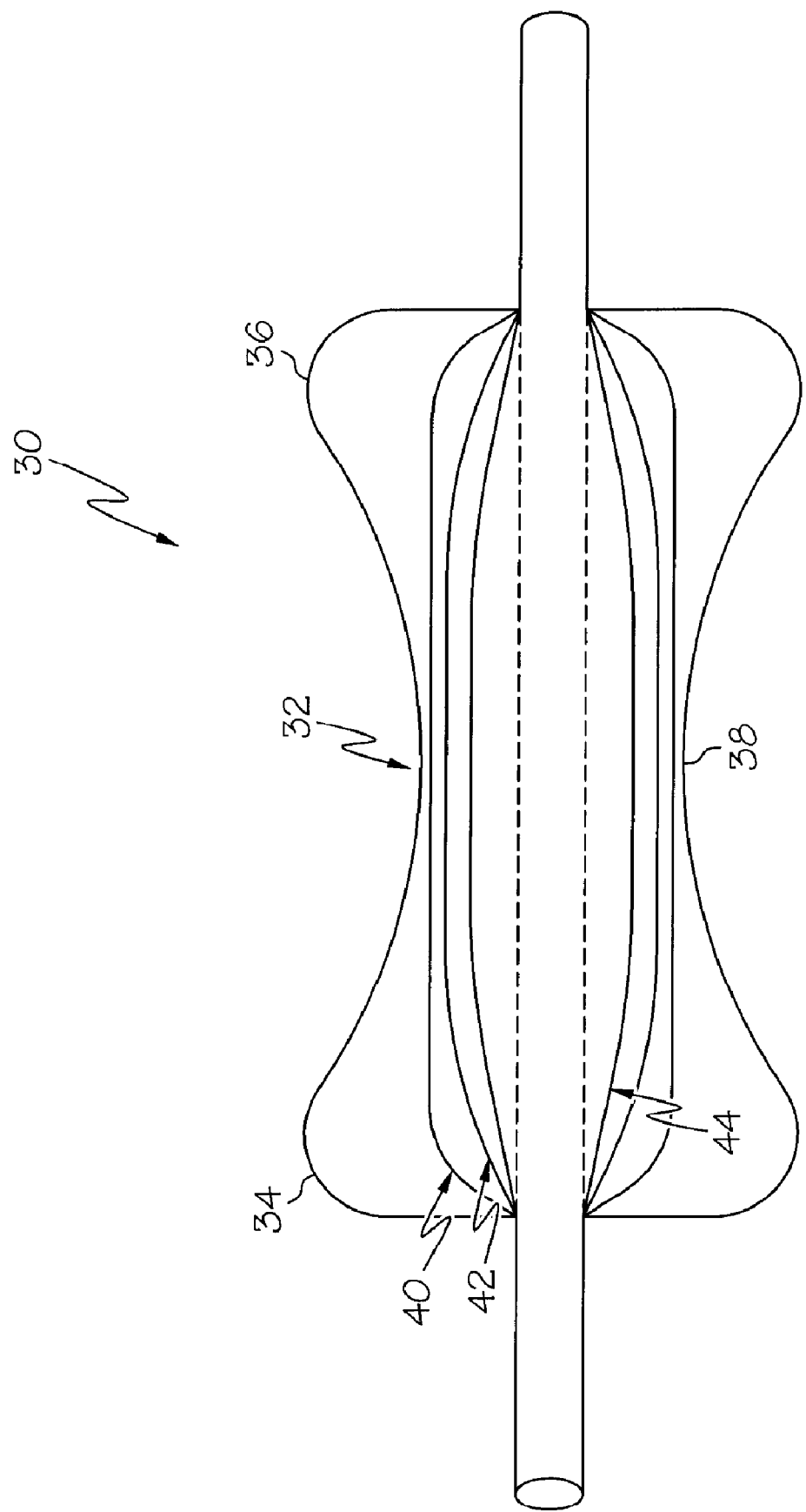
FIG. 2 is a perspective view of one embodiment of the balloon dilator in which the outer balloon has a dumbbell shape and multiple inner balloons.

As illustrated in FIG. 2, one embodiment of the invention is a balloon dilator apparatus 30 in which the inflatable outer balloon 32 is dumbbell-shaped. This dumbbell shape typically is created by making the proximal 34 and distal 36 ends of the balloon with a decreased balloon wall thickness as compared to the central section 38 of the balloon, which has a relatively increased balloon wall thickness. Alternatively, the central section 38 can have a flexible casing or layer of plastic or the like surrounding it (not shown), thereby preventing the central section 38 from dilating as quickly as the proximal and distal ends, 34, 36, yet still permitting complete inflation of the central section 38 at the higher inflation pressures. In another embodiment, the dumbbell shape can be obtained by forming the balloon from two or more different materials. For example, the proximal 34 and distal 36 ends of the balloon may be made from a more readily expandable plastic material than the central section 38 of the balloon.

The dumbbell shape prevents balloon slippage by inflating at either end (i.e. on either side of the stenosis) before the central section 38 inflates, and allows the central section 38 of the outer balloon 32 to stay in position over the stenosis during inflation. During inflation, the proximal 34 and distal 36 ends of the outer balloon 32 inflate first, forming the "dumbbell" shape, thereby trapping the stenotic airway segment at the central portion 38 of the balloon 32, so that the outer balloon 32 does not slip out of position. Then, as the pressure in the balloon is increased, the central portion 38 of the balloon fully inflates at the site of the stenosis.

The present invention can provide a balloon dilator with a rated burst pressure of up to 30 Atmospheres (atm). Generally, the larger the balloon diameter, the lower the burst pressure (e.g. for comparable Blue Max® angioplasty balloons, a 6.0 mm balloon has a rated burst pressure of 20 atm, while a 14.0 mm balloon has a rated burst pressure of 8 atm, and a 20.0 mm balloon has a rated burst pressure of 3.1 atm). To achieve this, the present invention provides an balloon which acts as an outer "sheath" that contains a series of inner balloons with smaller individual diameters that can tolerate a higher rated burst pressure than the outer balloon.

As shown in FIG. 2, the apparatus 30 can include a plurality of inner balloons 40, 42, 44. In the embodiment shown, inner balloon 44 is contained inside inner balloon 42, which is contained inside inner balloon 40. All of the inner balloons 40, 42, 44 are contained inside outer balloon 32, and are typically separately inflatable. Such an embodiment could be used with larger diameter outer balloons, e.g. between about 10 to about 20 mm. In this embodiment, the inner balloons 40, 42, 44 can be either dumbbell shaped or a "double cone" shape as seen with most angioplasty type balloons, and are inflated sequentially if higher pressures cannot be achieved by the outer balloon. Having a balloon dilator that incorporates multiple interconnected smaller balloons can achieve the desired pressure without risking balloon rupture during inflation. In another embodiment (not shown), the inner balloons 40, 42, 44 are all contained inside the outer balloon 32 but are not contained within one another. In this embodiment the inner balloons can be interconnected so that they all inflate simultaneously, like petals of a flower around the central core, within the outer balloon.

Figure 3:
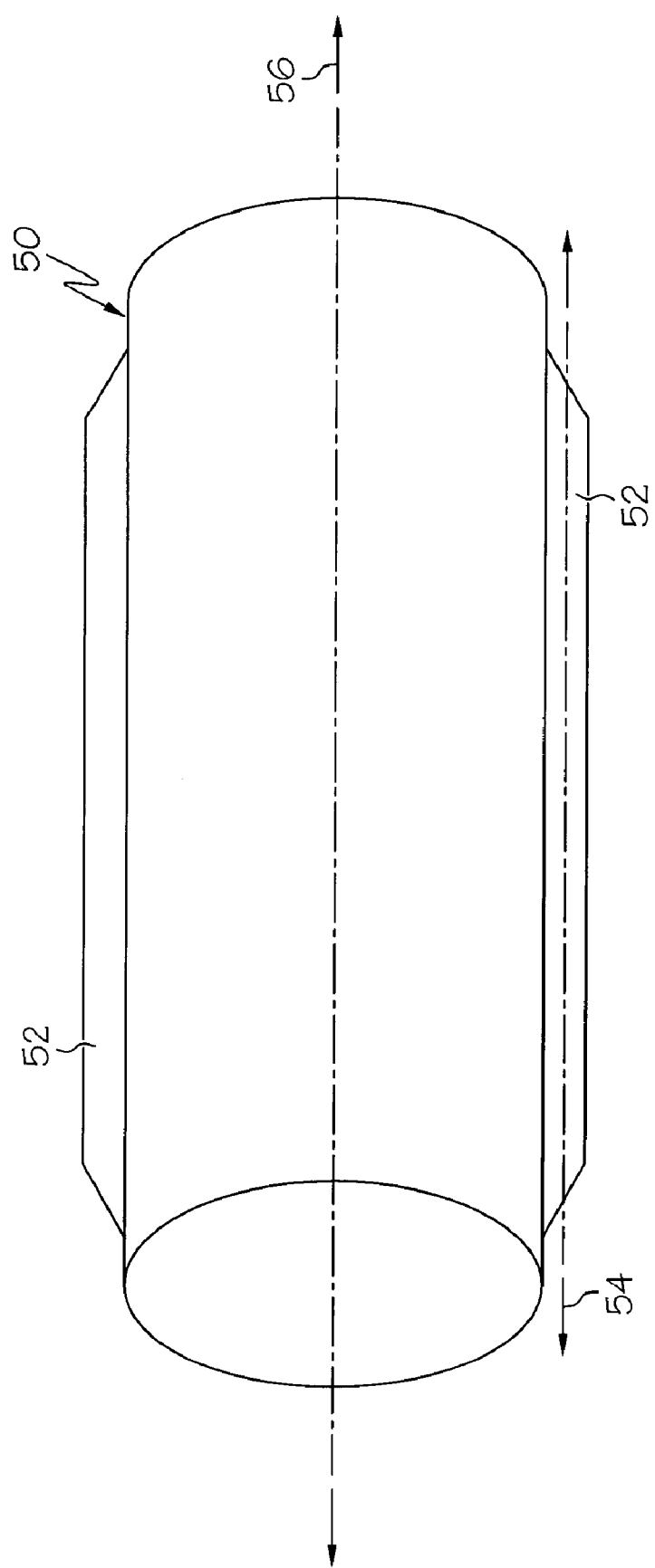
FIG. 3 is a perspective view of a flexible support member having microsurgical blades, the support member adapted to fit over the outer balloon according to one aspect of the invention.

As illustrated in FIG. 3, one embodiment of the invention can include a flexible support member 50 that can fit over the apparatus, specifically fitting over the outer balloon. The flexible support member 50 is typically made of a polyurethane material and includes a central axis 56 mounted along the central axis of the apparatus. The support member is adapted to fit over the external surface of the outer balloon, and is typically substantially compliant therewith during inflation and deflation. Support member 50 also includes at least one microsurgical blade, and in FIG. 3 two surgical blades 52 are attached. Blades 52 form an effective cutting edge upon inflation of the outer balloon. Blades 52 are typically made of stainless steel, and are elongated and permanently mounted on the flexible support member 50. In use, when the support member 50 is placed over the outer balloon, the blade axis 54 is parallel to the central axis 56 of the support member 50, which is substantially parallel to the central axis of the apparatus.

Having surgical blades 52 present on the apparatus during dilation typically permits controlled cutting or lysis of any scar tissue present in the patient's airway. The blades 52 should be clearly marked so that users can avoid inadvertently cutting themselves during placement of the support member 50 over the outer balloon. In one embodiment, the blades 52 lay flat on the surface of the support member prior to use and prior to inflation of the outer balloon 12, and then when the outer balloon reaches a certain pressure upon inflation the blades 52 will typically "stand up" or otherwise protrude or expose their cutting edge atop the flexible support member 50. Once fully deployed, the exposed edge of the blade 52 typically only protrudes between about 0.2 to about 0.4 mm, and the length of the blade is typically less than the length of the outer balloon 12. Typically there are a plurality of blades which are able to work together to embed into the stenosis or scar at a substantially uniform depth. For example, three blades could be permanently mounted on the flexible support member, each of the blades being separated from the other blades so that each blade is free to move from a relatively flat position to a cutting position on the flexible support member upon inflation of the outer balloon.

In practice, the balloon dilation procedure is typically performed at the site of a stenosis in the airway of a patient (i.e. the larynx, trachea or bronchi). Using the apparatus shown in FIG. 1, the surgeon or clinician first inserts the apparatus 10 into the airway, then advances the apparatus within the airway until the outer balloon 12 is across the stenosis. At this point, the surgeon or clinician inflates the outer balloon 12 to cause and allow the external surface 14 of the outer balloon 12 to expand upon and dilate the stenosis. To increase dilation pressures, the inner balloon 20 is then slowly inflated. Typically the inner balloon 20 is inflated after the inflation of the outer balloon 12. Under direct visualization, the balloons are typically inflated from between about 30 to about 120 seconds. The apparatus 10 can also be threaded over a guidewire (not shown) which fits through the hollow core 18 and is positioned across the stenosis. Repeat inflation-deflation cycles can be done if airway narrowing remains after the initial attempt.

During balloon dilation, the size of the balloon is first selected by the clinician, which depends upon the size of the stenosis in the patient's airway. The balloon size is typically between about 10 mm to about 40 mm in length. The outer balloon is positioned over the stenosis and then each balloon is individually dilated to the desired pressure with a balloon pump, typically to between about 8 to about 20 atmospheres. After these pressures are maintained for a predetermined period of time, typically between about 60 to about 180 seconds, the balloons are deflated and the clinician determines if repeat inflation is necessary. Repeat inflation can be safely performed if there is no obvious trauma to the airway.

While the balloon dilator of the present invention typically allows ventilation while inflated, the balloon dilator can also be manufactured without an inner hollow core for ventilation, but simply with a small lumen large enough to pass a guidewire. The advantage of such an embodiment is that the un-inflated balloon without a hollow core for ventilation is typically much "skinnier" and can pass through a very small hole (lumen) in the trachea or airway easier than a balloon dilator with a hollow core adapted to allow the patient to be ventilated therethrough.

While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. An apparatus for performing a balloon dilation procedure at the site of a stenosis or for deploying a stent in a patient, the apparatus comprising a central axis and an inflatable outer dumbbell-shaped balloon having an external surface, the apparatus being insertable into a lumen of a patient for movement of the balloon therein between a deflated configuration and an inflated configuration, wherein the dumbbell-shaped balloon has proximal and distal ends that have a decreased wall thickness as compared to the central section of the balloon, and wherein during inflation the balloon pressure is between about 3 atmospheres and about 30 atmospheres.

2. The apparatus according to claim 1, wherein when the dumbbell-shaped balloon is fully inflated it has a substantially uniform diameter from its proximal end to its distal end.

3. The apparatus according to claim 1, further comprising at least one inflatable inner balloon configured to inflate inside the dumbbell-shaped balloon yet separately from it.

4. The apparatus according to claim 3, comprising a plurality of inflatable inner balloons.

5. The apparatus according to claim 1, further comprising a flexible support member mounted along the central axis of the apparatus and on the external surface of the dumbbell-shaped balloon, the flexible support member being substantially compliant with the external surface of the balloon during movement therewith, and at least one microsurgical blade attached to the support member and adapted to form an effective cutting edge upon inflation of the balloon.

6. The apparatus according to claim 5, comprising a plurality of blades adapted to embed into the stenosis or the area in need of the stent at a substantially uniform depth.

7. The apparatus according to claim 5, wherein the support member is made of a polyurethane material and the at least one blade is made of stainless steel.

8. The apparatus according to claim 5, wherein the at least one blade includes a blade axis, the at least one blade being elongated and mounted on the support member with the blade axis substantially parallel to the central axis of the apparatus.

9. The apparatus according to claim 1, further comprising a hollow core adapted to allow the patient to be ventilated therethrough, said hollow core being only large enough to allow passage of a guidewire therethrough.

10. A method for performing a balloon dilation procedure at the site of a stenosis or for deploying a stent in a lumen of a patient, the method comprising the steps of:
    (1) inserting an apparatus into the lumen, the apparatus comprising a central axis and an inflatable outer dumbbell-shaped balloon having an external surface, the apparatus being insertable into the lumen of a patient for movement of the balloon therein between a deflated configuration and an inflated configuration, wherein the dumbbell-shaped balloon has proximal and distal ends that have a decreased wall thickness as compared to the central section of the balloon;
    (2) advancing the apparatus within the lumen until the dumbbell-shaped balloon is positioned within the area of the stenosis or the area in need of the stent; and
    (3) inflating the dumbbell-shaped balloon to cause and allow the external surface of the balloon to expand upon and dilate the area of the stenosis or the area in need of the stent, wherein during inflation the balloon pressure is between about 3 atmospheres and about 30 atmospheres.

11. The method according to claim 10, wherein when the dumbbell-shaped balloon is fully inflated it has a substantially uniform diameter from its proximal end to its distal end.

12. The method according to claim 10, wherein the apparatus further comprises a flexible support member mounted along the central axis of the apparatus and on the external surface of the dumbbell-shaped balloon, the flexible support member being substantially compliant with the external surface of the balloon during movement therewith, and at least one microsurgical blade attached to the support member and adapted to form an effective cutting edge upon inflation of the balloon, wherein the inflating step allows the at least one blade to form an effective cutting edge upon inflation of the balloon.

13. The method according to claim 12, wherein the flexible support member comprises a plurality of blades adapted to embed into the stenosis or the area in need of the stent at a substantially uniform depth.

14. The method according to claim 10, wherein the advancing step comprises the steps of:
    (i) inserting a guidewire into the lumen of the patient; and
    (ii) tracking the guidewire with the apparatus to position the dumbbell-shaped balloon across the stenosis or the area in need of the stent.

15. The method according to claim 10, further comprising the steps of:
    (4) deflating the dumbbell-shaped balloon after a predetermined amount of time;
    (5) repeating steps (1) through (4) if lumen narrowing remains after the initial attempt to dilate the stenosis or the area in need of the stent fails; and
    (6) removing the apparatus from the patient.

16. An apparatus for performing a balloon dilation procedure at the site of a stenosis or for deploying a stent in a patient, the apparatus comprising:
    a central axis;
    an inflatable dumbbell-shaped outer balloon having an external surface, wherein the dumbbell-shaped outer balloon has proximal and distal ends that have a decreased wall thickness as compared to the central section of the balloon;
    at least one inflatable inner balloon, wherein during inflation the balloon pressures are between about 3 atmospheres and about 30 atmospheres;

a flexible support member mounted along the central axis of the apparatus and on the external surface of the outer balloon, the flexible support member being substantially compliant with the external surface of the outer balloon during movement therewith; and at least one microsurgical blade attached to the support member and adapted to form an effective cutting edge upon inflation of the outer balloon, the apparatus being insertable into the lumen of a patient for movement of the balloons therein between a deflated configuration and an inflated configuration, the at least one inner balloon configured to inflate inside the outer balloon yet separately from the outer balloon, the dumbbell shape of the outer balloon adapted to hold the outer balloon in position over the site of the stenosis or the area in need of the stent, and the at least one blade adapted to form an effective cutting edge upon inflation of the outer balloon.

17. The apparatus according to claim 16, wherein the apparatus comprises a plurality of blades adapted to embed into the stenosis or the area in need of the stent at a substantially uniform depth.

18. The apparatus according to claim 16, wherein the support member is made of a polyurethane material and the at least one blade is made of stainless steel.

19. The apparatus according to claim 16, wherein the at least one blade includes a blade axis, the at least one blade being elongated and mounted on the support member with the blade axis substantially parallel to the central axis of the apparatus.

20. The apparatus according to claim 16, including a plurality of inflatable inner balloons, wherein all inner balloons are contained inside the outer balloon and are simultaneously inflatable within the outer balloon.

* * * * *